(12) United States Patent
Sullivan et al.

(10) Patent No.: US 8,425,443 B2
(45) Date of Patent: Apr. 23, 2013

(54) ELECTROMAGNETIC LOCKING MECHANISM FOR SUPPORTING LIMBS

(75) Inventors: Derek Sullivan, Bonita Springs, FL (US); Peter Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 191 days.

(21) Appl. No.: 13/105,374

(22) Filed: May 11, 2011

(65) Prior Publication Data

US 2011/0277773 A1 Nov. 17, 2011

Related U.S. Application Data (60) Provisional application No. 61/333,572, filed on May 11, 2010.

(51) Int. Cl.
*A61F 5/00* (2006.01)

(52) U.S. Cl.
USPC .............................................. 602/32; 128/845

(58) Field of Classification Search ................... 128/845, 128/878–879; 602/16, 20–28, 32–36; 601/46
See application file for complete search history.

(56) References Cited

U.S. PATENT DOCUMENTS

| | | | |
|---|---|---|---|
| 2,439,973 A | 4/1948 | Gunn | |
| 3,993,056 A * | 11/1976 | Rabischong et al. | 602/13 |
| 4,796,508 A | 1/1989 | Hoshino | |
| 4,807,618 A | 2/1989 | Auchinleck et al. | |
| 5,118,058 A | 6/1992 | Richter | |
| 5,314,174 A | 5/1994 | Hagman | |
| 5,857,492 A | 1/1999 | Salamun | |
| 6,371,425 B2 | 4/2002 | Fidler | |
| 6,491,273 B2 | 12/2002 | King et al. | |
| 2004/0030241 A1 * | 2/2004 | Green et al. | 600/422 |
| 2004/0167450 A1 * | 8/2004 | Buckman et al. | 602/23 |
| 2007/0282311 A1 | 12/2007 | Scott et al. | |
| 2008/0097269 A1 * | 4/2008 | Weinberg et al. | 602/16 |

* cited by examiner

*Primary Examiner* — Michael A. Brown
(74) *Attorney, Agent, or Firm* — Akerman Senterfitt; Michael K. Dixon (57) ABSTRACT

A limb support system for supporting one or more limbs of a patient during surgery is disclosed. The limb support system may include one or more joints formed from electromagnets that move locking mechanisms between locked and unlocked positions to enable a patient's limb to be supported in a desired position. At least one of the joints may be supported by a support arm that is attached to support structure. A limb support device, such as, but not limited to, an armrest or a wrist support may be attached to the housing of the joint.

20 Claims, 7 Drawing Sheets

ELECTROMAGNETIC LOCKING MECHANISM FOR SUPPORTING LIMBS

CROSS-REFERENCE TO RELATED APPLICATION

This patent application claims the benefit of U.S. Provisional Patent Application No. 61/333,572, filed May 11, 2010, which is incorporated by reference in its entirety.

FIELD OF THE INVENTION

The present invention relates in general to patient support systems and, more particularly, to patient support systems useful for supporting the limbs of patients during surgery.

BACKGROUND

While recovering from an injury or from surgery, patients often have their limbs secured in position to enhance the healing process. In addition, patients often have one or more of their limbs secured during surgery to prevent movement of the limb. Often times, the limb is secured in close proximity to a bed surface enabling a patient to lay down on a bed surface and have their limb secured. Currently, there exist devices for securing a patient's limbs above the patient while the patient lies on the bed. However, the devices typically have a limited range of motion and are often awkward to secure while retaining the patient's limb in the desired position. Thus, a need exists for a more effective limb support system.

SUMMARY OF THE INVENTION

This invention is directed to a limb support system for supporting one or more limbs of a patient during surgery. The limb support system may be configured to support one or more patient's limbs such that when the patient is unconscious during surgery, the limb is not moved and remains stable. The limb support system may support a limb of a patient while the patient is in a seated, prone or other position. Components of the limb support system may be quickly moved between locked and unlocked positions so that the limb support system may be quickly positioned correctly relative to a patient to support the patient's limb, such as an arm, a leg, a hand, a finger or other body part in a specific desired position.

The limb support system may be formed from at least one joint configured to rotate about at least two axes that are orthogonal to each other. In at least one embodiment, two or more joints may be coupled together via support arms in series to create additional flexibility and ease of use. One or more joints may be formed from a first electromagnet and a biasing device positioned generally opposite to each other. One or more first locking members may be positioned between the first electromagnet and the biasing device. The first locking member may be movable between a first locked position and a second unlocked position that enables rotation about a first axis. A second locking member may be in mechanical connection with the first locking member. The second locking member may be positioned proximal to the first electromagnet and opposite to the first locking member. The second locking member may be configured to control rotation about a second axis that is orthogonal to the first axis. One or more support arms may extend from the joint and may be coupled to a support structure to support the joint.

In one embodiment, the biasing device may be a second electromagnet. In another embodiment, the biasing device may be a spring configured to bias the at least one first locking member towards biasing device. The first locking member may be formed from a rotation control plate and a stationary locking ring with internal teeth that mesh with teeth of the rotation control plate. The stationary locking ring may be coupled to a lower housing. The second locking member may be formed from one or more pads having teeth configured to engage teeth extending from a rotating gear coupled to a locking rod that is concentric with the second axis. The pad may be movable between a locked position in which the pad is in contact with the rotating gear and an unlocked position in which the pad is not in contact with the rotating gear. The pad may be positioned generally tangential to an outer tip of a tooth extending from the rotating gear.

The joint may also include a housing formed from first and second subhousings. The first subhousing may encase the first locking member and may be rotatable about the first axis relative to the second subhousing. The second subhousing may encase the second locking member and may be rotatable about the second axis such that the first and second subhousings rotate together about the second axis. In one embodiment, the first and second subhousings may be generally cylindrical. The first subhousing may be formed from a lower housing and a stationary locking ring of the first locking member. The outer surfaces of the lower housing and the stationary locking ring may be flush with each other.

An advantage of the limb support system is that the limb support system enables a patient's limb to be supported in any position.

Another advantage of the limb support system is that the limb support system may be placed into an unlocked position in which the a patient's limb attached to the support arm may be moved into any position and then secured quickly in that position by activating the first electromagnet to create a locked position.

These and other embodiments are described in more detail below.

BRIEF DESCRIPTION OF THE DRAWINGS

The accompanying drawings, which are incorporated in and form a part of the specification, illustrate embodiments of the presently disclosed invention and, together with the description, disclose the principles of the invention.

DETAILED DESCRIPTION OF THE INVENTION

Figure 2:
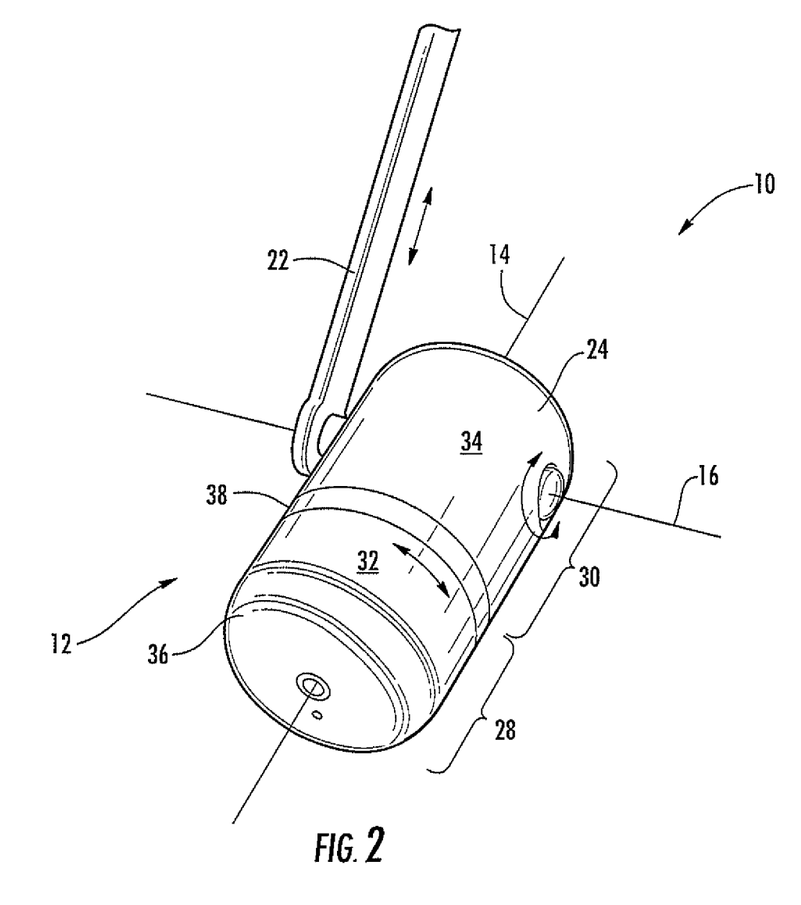
FIG. 2 is another partial perspective view of the limb support system.
Figure 3:
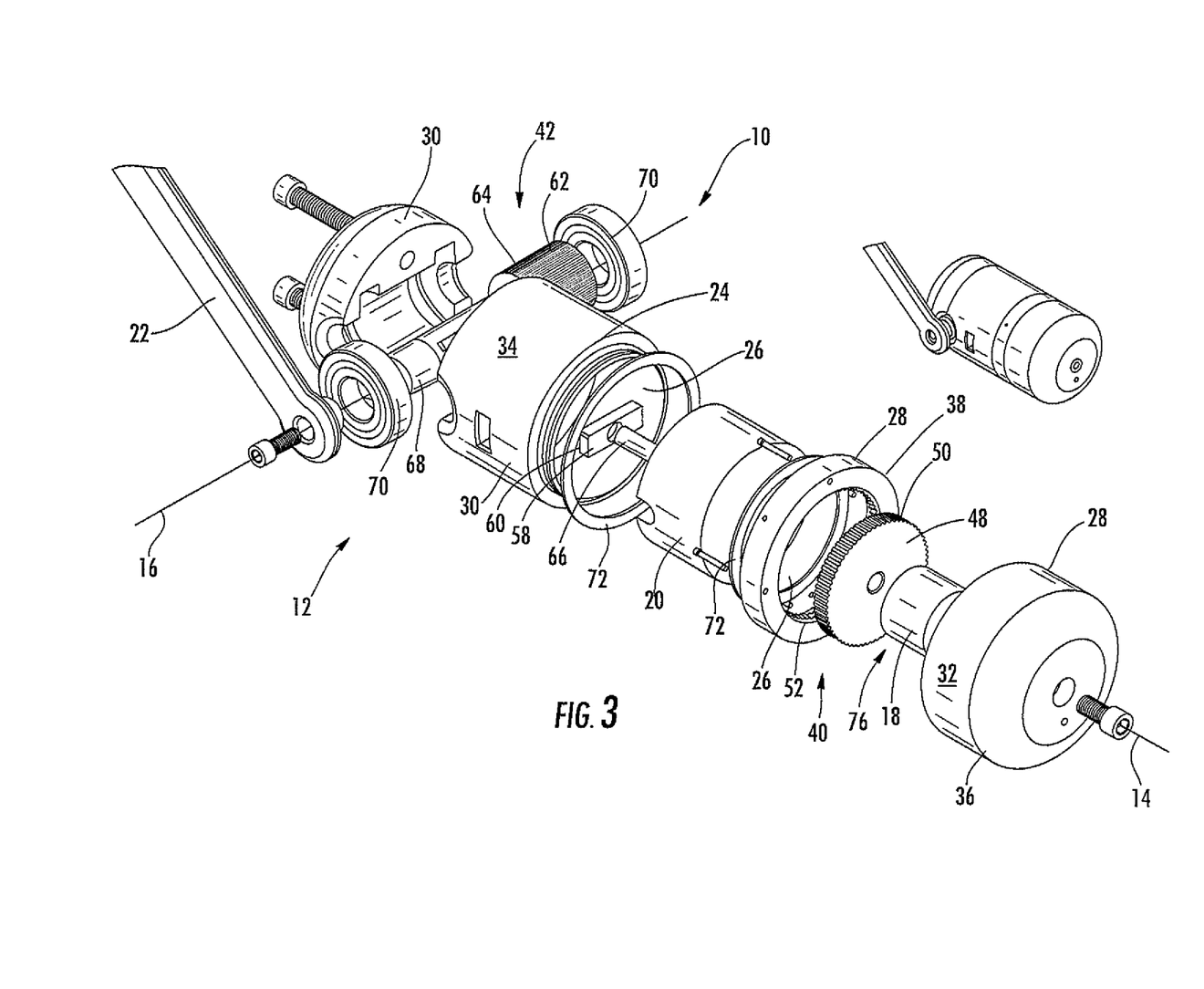
FIG. 3 is an exploded view of a joint of the limb support system.
Figure 4:
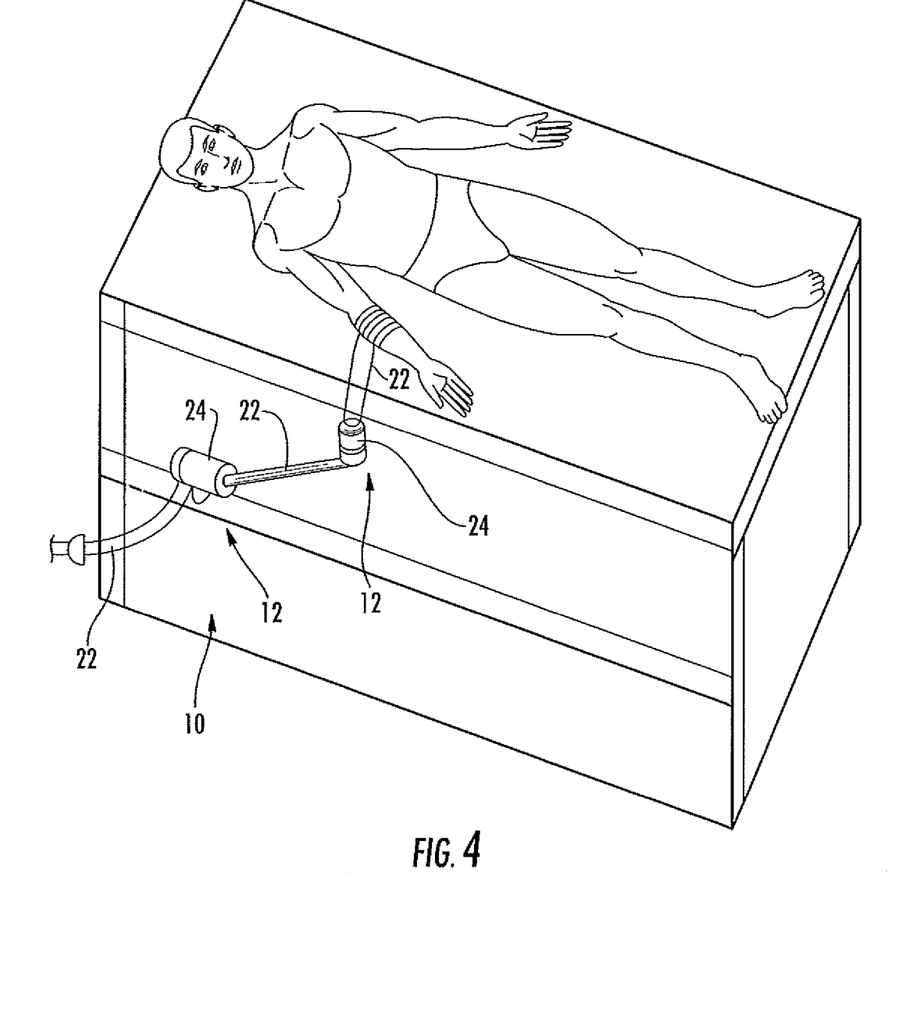
FIG. 4 is sketch of the limb support system in use.
Figure 5:
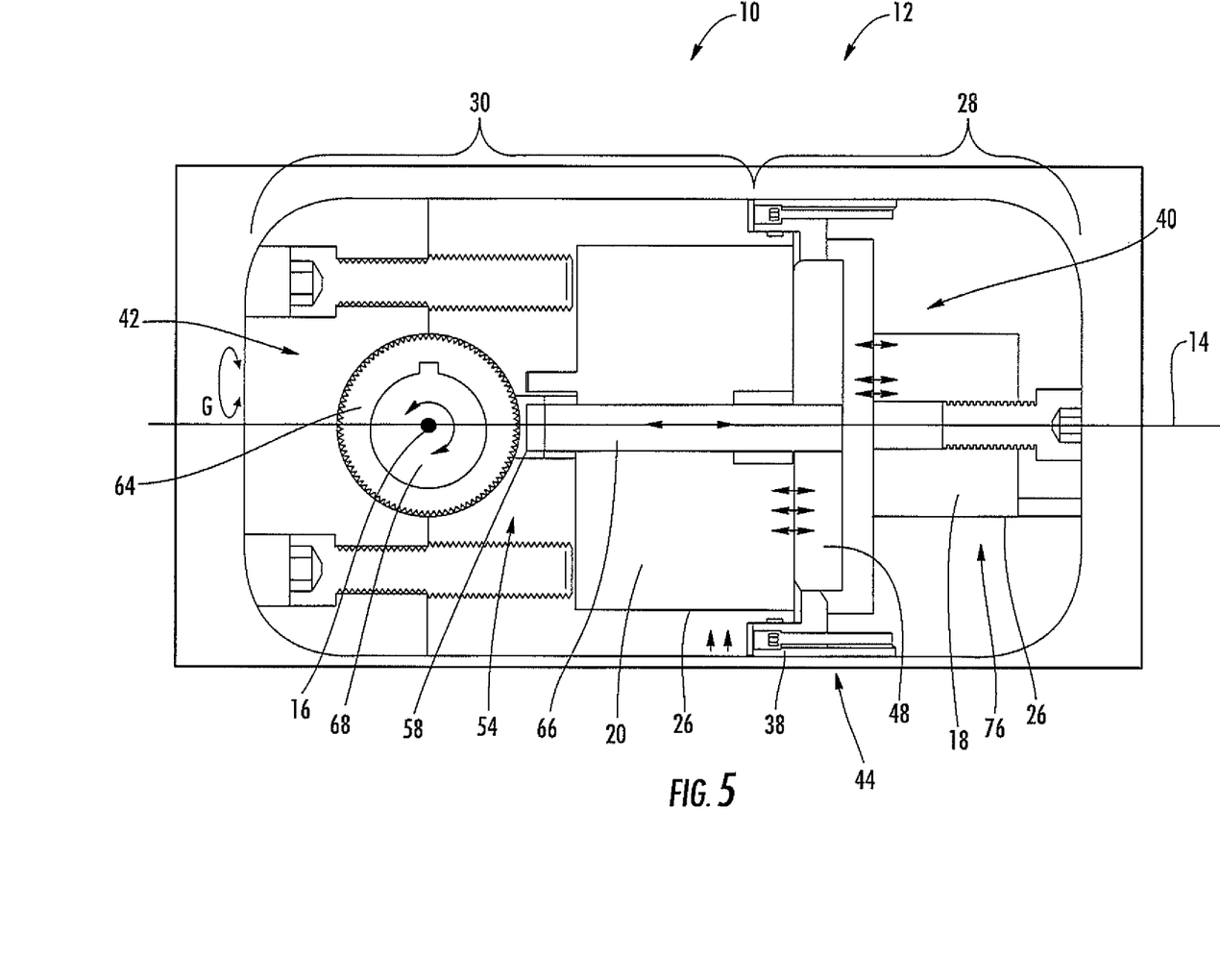
FIG. 5 is a cross-sectional view of a joint in a locked position taken along section line 5-5 in FIG. 1.
Figure 6:
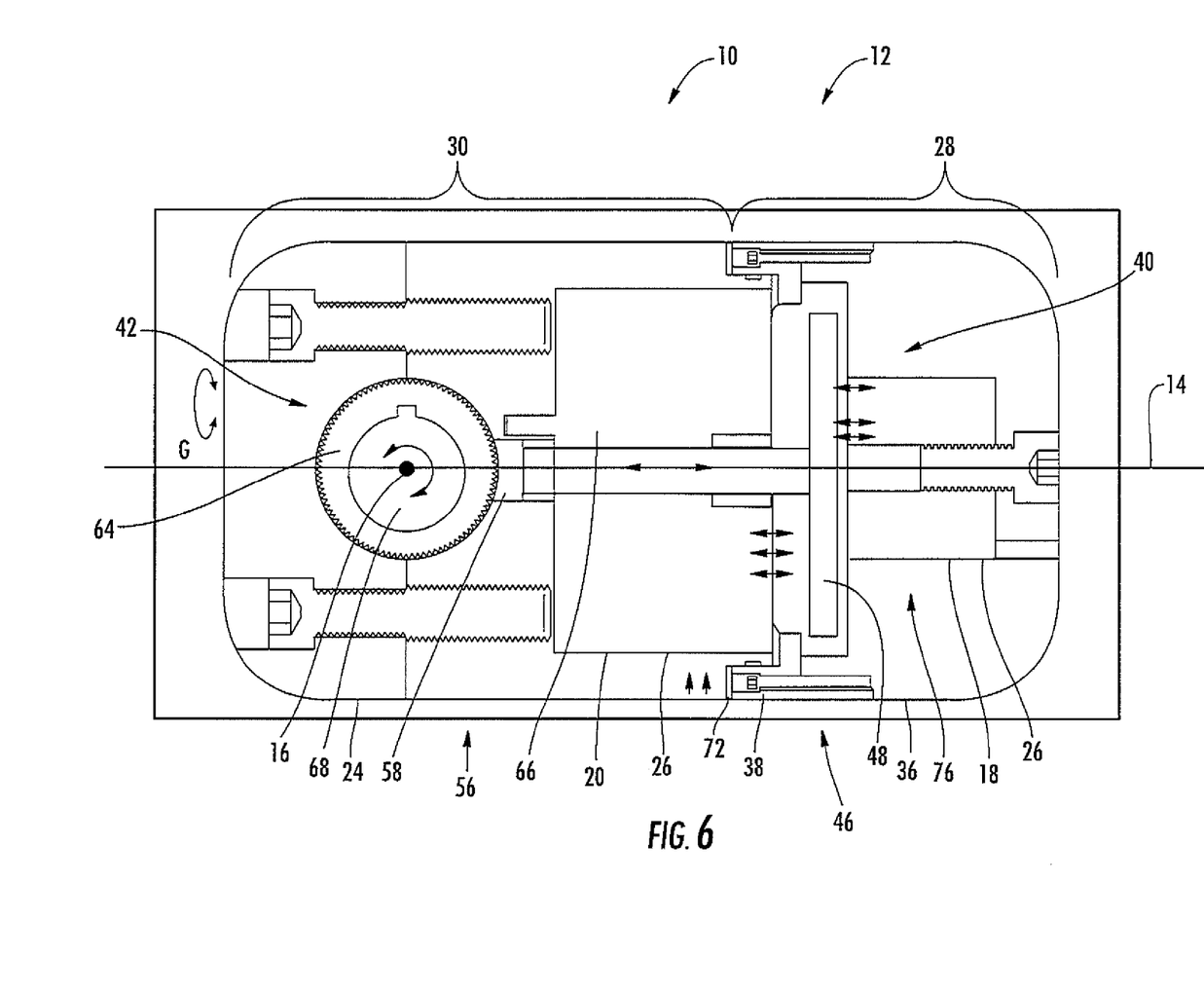
FIG. 6 is a cross-sectional view of a joint in an unlocked position taken along section line 6-6 in FIG. 1.

As shown in FIGS. 1-7, a limb support system 10 for supporting one or more limbs of a patient during surgery is disclosed. The limb support system 10 may be configured to support a patient's limb such that when a patient is unconscious during surgery, the limb is not moved and remains stable. The limb support system 10 may support a limb of a patient while the patient is in a seated, prone or other position. Aspects of the limb support system 10 may be quickly moved between locked and unlocked positions, as shown in FIGS. 5 and 6 respectively, so that the limb support system 10 may be quickly positioned correctly relative to a patient to support the patient's limb, such as an arm, a leg, a hand, a finger or other body part, as shown in FIG. 4.

Figure 1:
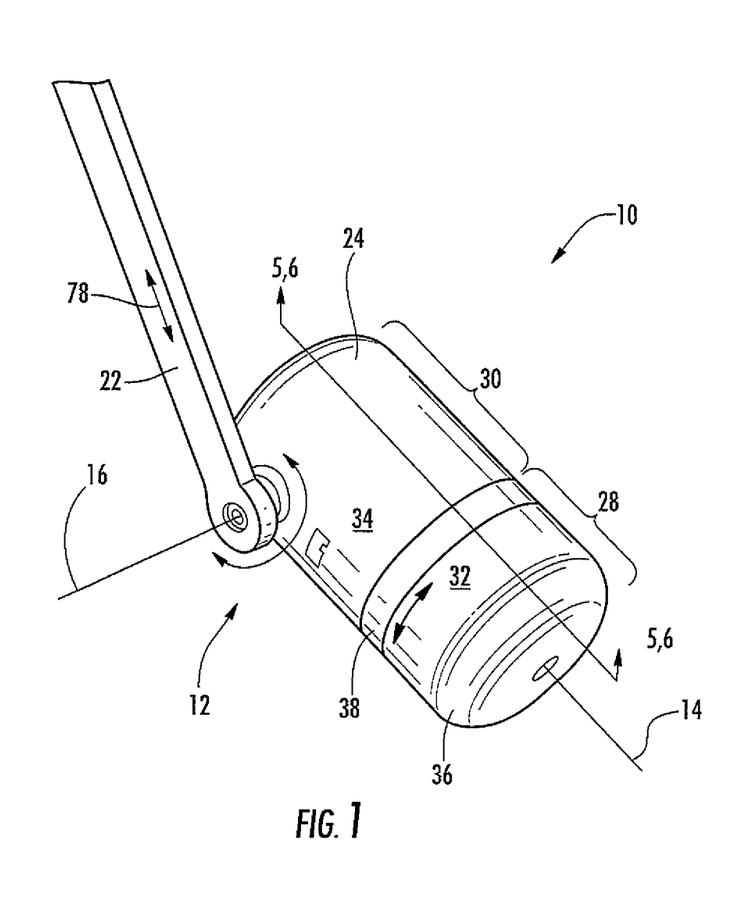
FIG. 1 is partial perspective view of a limb support system.

The limb support system 10 may be formed from one or more joints 12 that enable a limb to be adequately supported. In at least one embodiment, the joint 12 may be configured to rotate about at least two axes 14, 16 that are orthogonal to each other, as shown in FIGS. 1 and 2. The joint 12 may include a first electromagnet 20 and a biasing device 76. In at least one embodiment, the biasing device 76 may be a second electromagnet 18. The first and second electromagnets 20, 18 may be generally aligned and may be positioned generally opposite to each other, as shown in FIG. 3. The first and second electromagnets 20, 18 may have any appropriate size and configuration. In at least one embodiment, as shown in FIG. 3, the first and second electromagnets 20, 18 may be generally cylindrical. The first electromagnet 20 may control rotation of the entire joint 12 about a support arm 22 and thus may have a stronger electromagnet than the secured electromagnet 18. The first electromagnet 20 may be larger in size than the second electromagnet 18. A housing 24 of the limb support system 10 may be configured to contain the first and second electromagnets 20, 18 within chambers 26 in the housing 24.

The housing 24 may be formed from first and second subhousings 28, 30. The first and second subhousings 28, 30 may be separated by one or more PTFE rings 72. The PTFE rings 72 may provide a low friction sliding surface. The first subhousing 28 may be rotatable about the first axis 14 relative to the second subhousing 30. The first and second subhousings 28, 30 may be generally cylindrical. Outer surfaces 32, 34 of the first and second subhousings 28, 30 may be generally flush with each other. In other embodiments, the outer surfaces 32, 34 may have alternative configurations. The first subhousing 28 may be formed from a lower housing 36 and a stationary locking ring 38 that forms a portion of a first locking member 40. The lower housing 36 and the stationary locking ring 38 may be coupled together with one or more mechanical connectors, such as, but not limited to, bolts, screws and other appropriate articles. Outer surfaces 32 of the lower housing 36 and the stationary locking ring 38 may be flush, as shown in FIGS. 1 and 2. The first subhousing 28 may encase the first locking member 40 and the second electromagnet 18 as shown in FIG. 3. The second subhousing 30 may encase a second locking member 42 and the first electromagnet 20 and may be rotatable about the second axis 16 such that the first and second subhousings 28, 30 rotate together about the second axis 16.

Figure 7:
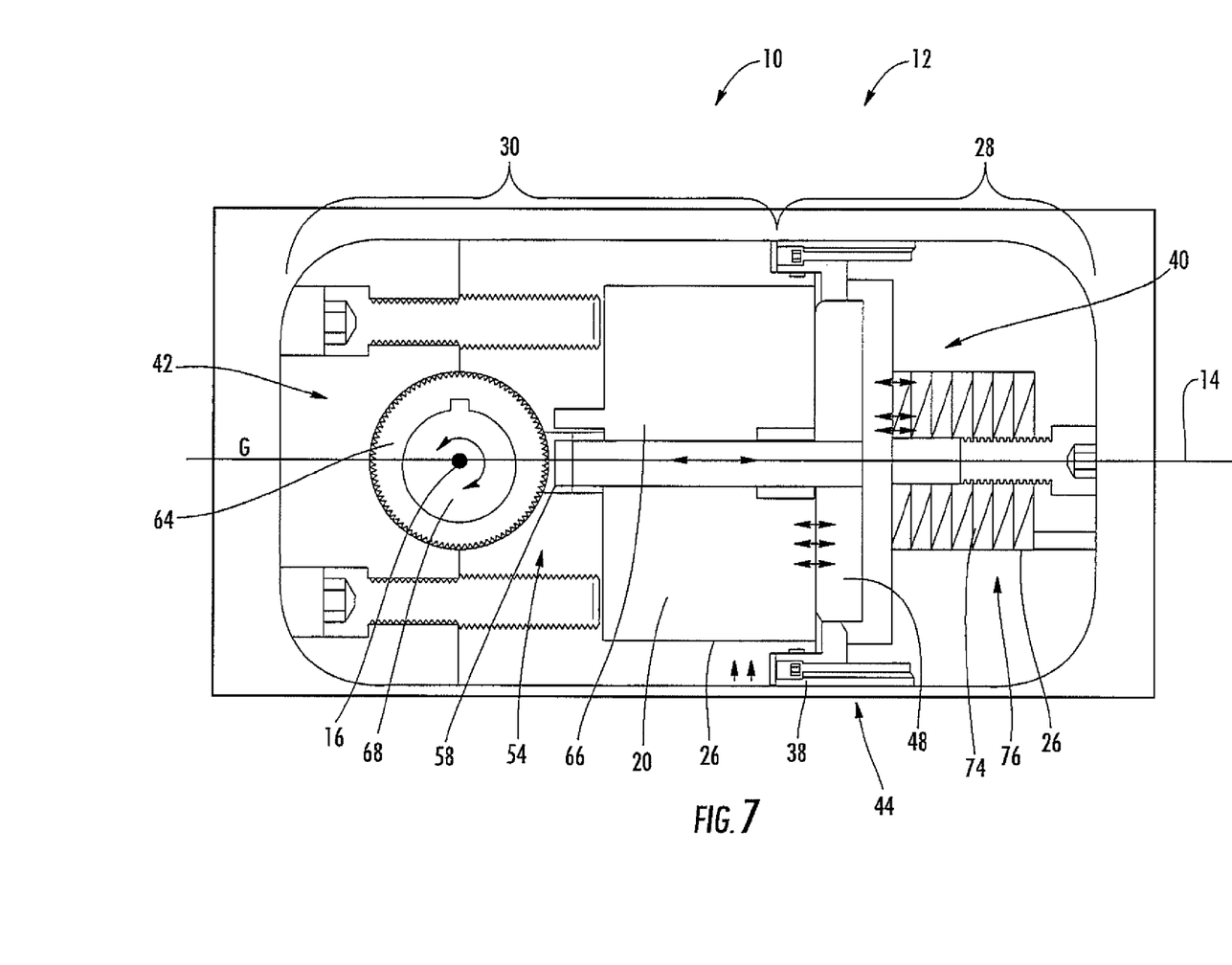
FIG. 7 is a cross-sectional view of an alternative configuration of the joint in the locked position taken along section line 5-5 in FIG. 1.

The limb support system 10 may include one or more first locking members 40 positioned in between the first and second electromagnets 20, 18. The first locking member 40 may be movable between a first locked position 44, as shown in FIG. 5, and a second unlocked position 46 that enables rotation about the first axis 14, as shown in FIG. 6. The first locking member 40 may move linearly away from the second electromagnet 18. The first locking member 40 may be formed from the stationary locking ring 38 and a rotation control plate 48, as shown in FIG. 3. The rotation control plate 48 may include one or more teeth 50 extending radially outward from the rotation control plate 48 that are configured to mesh with teeth 52 extending inward from the stationary locking ring 38. When the rotation control plate 48 is positioned in the stationary locking ring 38 through use of the first and second electromagnets 20, 18, the first subhousing 28 is prevented from rotating about the first axis 14 relative to the second subhousing 30, as shown in FIG. 5. In an alternative embodiment, as shown in FIG. 7, the rotation control plate 48 may be positioned in the stationary locking ring 38 through use of a biasing device 76 and the first electromagnet 20. In at least one embodiment, the biasing device may be a spring 74. The spring 74 may have any appropriate configuration.

The limb support system 10 may include a second locking member 42 in mechanical connection with the first locking member 40, as shown in FIG. 3. The second locking member 42 may control rotation about the second axis 16, which may be generally orthogonal to the first axis 14. The second locking member 42 may move between a locked position 54, shown in FIG. 5, and an unlocked position 56, shown in FIG. 6. In the locked positioned shown in FIG. 5, rotation of the housing 24, including the first and second subhousings 28, 30 about the second axis 16 is prevented. Conversely, in the unlocked position shown in FIG. 6, rotation of the housing 24, including the first and second subhousings 28, 30 about the second axis 16 is permitted. The pad 58 may be disengaged from the teeth 62 on the rotating gear 64, and the rotation control plate 48 may be positioned proximal to the first electromagnet 18.

In one embodiment shown in FIG. 3, the second locking member 42 may be formed from one or more pads 58 having teeth 60 configured to engage teeth 62 extending from a rotating gear 64 coupled to a pinion gear shaft 68 that is concentric with the second axis 16. The pad 58 may be coupled to locking rod 66 and be movable between the locked position 54 in which the pad 58 is in contact with the rotating gear 64 and an unlocked position 56 in which the pad 58 is not in contact with the rotating gear 64. Movement of the rotation control plate 48 causes the locking rod 66 to move axially and move the pad 58. The pad 58 may be positioned generally tangential to an outer tip of a tooth 62 extending from the rotating gear 64. The pad 58 may have any appropriate configuration. Confining the pad 58 within a cavity having a shape that is the same as that of the pad 58 prevents rotation about the axis 14 depending on whether the rotation control plate 48 is locked within the stationary locking ring 38.

In at least one embodiment, the rotating gear 64 may be coupled to and concentric with a pinion gear shaft 68. The pinion gear shaft 68 may be supported by one or more bearings 70. As shown in FIG. 3, the pinion gear shaft 68 may be supported by a bearing 70 at each end of the pinion gear shaft 68. The bearings 70 may be held in position with chambers formed into the second subhousing 30. The second subhousing 30 may be formed from two pieces that are configured to be joined together by being joined around the pinion gear shaft 68.

The pinion gear shaft 68 may also be attached to the support arm 22 through any appropriate way, such as, but not limited to, a bolt, screw or other mechanical connector. The support arm 22 may be coupled to a support structure to support the joint 12. The support arm 22 may have any appropriate size and configuration and may be formed from any appropriate material such as, but not limited to, metal and plastic. The support arm 22 may be extendable such that the joint 12 may be moved axially as shown with arrows 78 in FIGS. 1 and 2.

The limb support system 10 has been described as having a support arm 22 coupled to a joint 12. The support system 10 may include multiple such configurations including multiple support arm 22 and joint 12 combinations coupled together in series to meet the specific needs of a patient in surgery, as shown in FIG. 4. For instance, the limb support system 10 may have a limb support, an arm support, a hand support, a finger support, a foot support, an ankle support, a leg support, or other such device coupled to the housing 24 for ergonomically supporting a limb or a portion of a limb of a patient. The additional joints 12 increase the degrees of freedom about three axes. In another alternative embodiment, a third and fourth electromagnet may be positioned between 68 and 22. The electromagnets may be smaller in size than first and second electromagnets 20, 18 and may be rotatable about the axis 10. The electromagnets may permit telescoping motion of arm 22 by using a similar concept of having a plate that falls into a slot with teeth.

The limb support system 10 may be used to control position of a patient's limb during surgery. In particular, aspects of the limb support system 10 may be moved between locked and unlocked positions so that a limb may be positioned as desired and held in that position throughout surgery. The housing 24 and joint 12 may move axially with the support arm 22 moving telescopically. When the larger, first electromagnet 20 is activated and the smaller, second electromagnet 18 is deactivated, as shown in FIG. 5, the rotation control plate 48 is drawn into contact with the larger first electromagnet 20. In this position, the teeth 50 extending from the rotation control plate 48 engage the teeth 52 extending inwardly from the stationary locking ring 38 and place the first subhousing 28 in a locked position relative to the second subhousing 30. Simultaneously, the pad 58 engages the rotating gear 64 and prevents the second subhousing 30 from rotating around the pinion gear shaft 68. When the larger, first electromagnet 20 is deactivated and the smaller, second electromagnet 18 is activated, as shown in FIG. 6, the rotation control plate 48 is drawn towards the smaller, second electromagnet 18 and out of contact with the larger first electromagnet 20 and with the stationary locking ring 38. As such, the pad 58 is moved out of contact with the rotating gear 64, thereby permitting rotating of the first and second subhousings 28, 30 together about the second axis 16. The rotation control plate 48 is moved axially such that the teeth 50 extending from the rotation control plate 48 are removed from being in contact with the teeth 52 extend from the stationary locking ring 38. As such, the first subhousing 28 is rotatable about the first axis 14 relative to the second subhousing 30.

The foregoing is provided for purposes of illustrating, explaining, and describing embodiments of this invention. Modifications and adaptations to these embodiments will be apparent to those skilled in the art and may be made without departing from the scope or spirit of this invention or the following claims.

We claim:

1. A limb support system, comprising:
   at least one joint configured to rotate about at least two axes that are orthogonal to each other, the at least one joint, comprising:
      a first electromagnet and a biasing device positioned generally opposite to each other with at least one first locking member positioned in between the first electromagnet and the biasing device, wherein the at least one first locking member is movable between a first locked position and a second unlocked position that enables rotation about a first axis; and
      a second locking member in mechanical connection with the first locking member, wherein the second locking member is positioned proximal to the first electromagnet and opposite to the first locking member, wherein the second locking member is configured to control rotation about a second axis that is orthogonal to the first axis; and
   at least one support arm extending from the joint and coupled to a support structure to support the at least one joint.

2. The limb support system of claim 1, wherein the biasing device is a second electromagnet.

3. The limb support system of claim 1, wherein the biasing device is a spring configured to bias the at least one first locking member towards biasing device.

4. The limb support system of claim 1, wherein the at least one first locking member is comprised of a rotation control plate and a stationary locking ring with internal teeth that mesh with teeth of the rotation control plate.

5. The limb support system of claim 4, wherein the stationary locking ring is coupled to a lower housing.

6. The limb support system of claim 1, wherein the second locking member is formed from at least one pad having teeth configured to engage teeth extending from a rotating gear coupled to a locking rod that is concentric with the second axis and wherein the at least one pad is movable between a locked position in which the at least one pad is in contact with the rotating gear and an unlocked position in which the at least one pad is not in contact with the rotating gear.

7. The limb support system of claim 6, wherein the at least one pad is positioned generally tangential to an outer tip of a tooth extending from the rotating gear.

8. The limb support system of claim 1, wherein the joint further comprises a housing formed from first and second subhousings, wherein the first subhousing encases the first locking member and is rotatable about the first axis and relative to the second subhousing, and the second subhousing encases the second locking member and is rotatable about the second axis such that the first and second subhousings rotate together about the second axis.

9. The limb support system of claim 8, wherein the first and second subhousings are generally cylindrical.

10. The limb support system of claim 9, wherein first subhousing is formed from a lower housing and a stationary locking ring of the first locking member, wherein the outer surfaces of the lower housing and the stationary locking ring are flush with each other.

11. A limb support system, comprising:
   at least one joint configured to rotate about at least two axes that are orthogonal to each other, the at least one joint, comprising:
      first and second electromagnets positioned generally opposite to each other with at least one first locking member positioned in between the first and second electromagnets, wherein the at least one first locking member is movable between a first locked position and a second unlocked position that enables rotation about a first axis; and
      a second locking member in mechanical connection with the first locking member, wherein the second locking member is positioned proximal to the first electromagnet and opposite to the first locking member, wherein the second locking member is configured to control rotation about a second axis that is orthogonal to the first axis;
   at least one support arm extending from the joint and coupled to a support structure to support the at least one joint; and
   wherein the joint further comprises a housing formed from first and second subhousings, wherein the first subhousing encases the first locking member and is rotatable about the first axis and relative to the second subhousing, and the second subhousing encases the second locking member and is rotatable about the second axis such that the first and second subhousings rotate together about the second axis.

12. The limb support system of claim 11, wherein the at least one first locking member is comprised of a rotation control plate and a stationary locking ring with internal teeth that mesh with teeth of the rotation control plate.

13. The limb support system of claim 12, wherein the stationary locking ring is coupled to a lower housing.

14. The limb support system of claim 11, wherein the second locking member is formed from at least one pad having teeth configured to engage teeth extending from a rotating gear coupled to a locking rod that is concentric with the second axis and wherein the at least one pad is movable between a locked position in which the at least one pad is in contact with the rotating gear and an unlocked position in which the at least one pad is not in contact with the rotating gear.

15. The limb support system of claim 14, wherein the at least one pad is positioned generally tangential to an outer tip of a tooth extending from the rotating gear.

16. The limb support system of claim 15, wherein the first and second subhousings are generally cylindrical.

17. The limb support system of claim 16, wherein first subhousing is formed from a lower housing and a stationary locking ring of the first locking member, wherein the outer surfaces of the lower housing and the stationary locking ring are flush with each other.

18. A limb support system, comprising:
at least one joint configured to rotate about at least two axes that are orthogonal to each other, the at least one joint, comprising:
first and second electromagnets positioned generally opposite to each other with at least one first locking member positioned in between the first and second electromagnets, wherein the at least one first locking member is movable between a first locked position and a second unlocked position that enables rotation about a first axis; and
a second locking member in mechanical connection with the first locking member, wherein the second locking member is positioned proximal to the first electromagnet and opposite to the first locking member, wherein the second locking member is configured to control rotation about a second axis that is orthogonal to the first axis;
at least one support arm extending from the joint and coupled to a support structure to support the at least one joint;
wherein the joint further comprises a housing formed from first and second subhousings, wherein the first subhousing encases the first locking member and is rotatable about the first axis and relative to the second subhousing, and the second subhousing encases the second locking member and is rotatable about the second axis such that the first and second subhousings rotate together about the second axis;
wherein the at least one first locking member is comprised of a rotation control plate and a stationary locking ring with internal teeth that mesh with teeth of the rotation control plate; and
wherein the second locking member is formed from at least one pad having teeth configured to engage teeth extending from a rotating gear coupled to a locking rod that is concentric with the second axis and wherein the at least one pad is movable between a locked position in which the at least one pad is in contact with the rotating gear and an unlocked position in which the at least one pad is not in contact with the rotating gear.

19. The limb support system of claim 18, wherein the at least one pad is positioned generally tangential to an outer tip of a tooth extending from the rotating gear.

20. The limb support system of claim 18, wherein the first and second subhousings are generally cylindrical, wherein first subhousing is formed from a lower housing and a stationary locking ring of the first locking member, and wherein the outer surfaces of the lower housing and the stationary locking ring are flush with each other.

* * * * *